United States Patent [19]

Pitts, Jr. et al.

[11] Patent Number: 5,019,557

[45] Date of Patent: May 28, 1991

[54] METHOD FOR THE EFFECTIVE TREATMENT OF DISEASE CONDITIONS IN HUMANS ASSOCIATED WITH HTLV-III INFECTION

[76] Inventors: Ferris N. Pitts, Jr., 3500 E. California, Pasadena, Calif. 91107; Allen D. Allen, 11900 Louise Ave., Granada Hills, Calif. 91344

[21] Appl. No.: 378,497

[22] Filed: Jul. 10, 1989

Related U.S. Application Data

[63] Continuation of Ser. No. 243,198, Sep. 8, 1988, abandoned, which is a continuation of Ser. No. 907,363, Sep. 15, 1986, abandoned.

[51] Int. Cl.$^5$ .................. A61K 37/02; B28B 1/26; B28B 21/08; B28B 21/36
[52] U.S. Cl. .......................... 514/2; 514/21; 424/85.1; 424/86; 424/88; 424/89
[58] Field of Search .................. 424/85.1, 86, 88, 89; 514/2, 21

[56] References Cited

U.S. PATENT DOCUMENTS

| | | | |
|---|---|---|---|
| 4,070,454 | 1/1978 | Relyveld | 424/89 |
| 4,165,370 | 8/1979 | Coval | 424/86 |
| 4,276,283 | 6/1981 | Eibl et al. | 424/86 |
| 4,477,432 | 10/1984 | Hardie | 424/86 |
| 4,482,483 | 11/1984 | Curry et al. | 424/85 |
| 4,520,113 | 5/1985 | Gallo et al. | 436/504 |
| 4,647,773 | 3/1987 | Gallo et al. | 424/89 |
| 4,659,563 | 4/1987 | Dobkin | 424/86 |
| 4,665,159 | 5/1987 | Dobkin | 424/86 |
| 4,692,403 | 9/1987 | Lindner et al. | 424/86 |
| 4,714,613 | 12/1987 | Shouval et al. | 424/86 |

OTHER PUBLICATIONS

Abstract Th. B. P. 118 Vardinon et al., "HIV-Infected Subjects Respond to Polio Vaccination Booster According to Absolute T4 Cell Count" V$^{th}$ International Conference on AIDS, Montreal, Canada, Jun. 4–9, 1989.

American College of Physicians (1985) Guide for Adult Immunization pp. ix–xii, 1–3, 17, 20–21, 24–25, 43–49, 55–57, 70–72 Appendix(1),(2)(3)(4)(5)(6)(7), pp. 93–125.

Fulginiti, V. Active "Immunization for Infectious Diseases", pp. 83–100(1979), in Conn, H. F. (Ed) Current Therapy (1979) W. B. Saunders Co. Phila., PA.

Gershon, A. "Immunization Practice" (1982), pp. 601–604, in Gellis, S.S. (ed.) Current Pediatric Therapy-10, W. B. Saunders Co., Phila., PA.

Ogra, P. L. et al. "Implications of Secretory Immune System in Virus Infection" pp. 271–282(1974) in J. Mestecky (ed.), "The Immunoglobulin A System" Plenum Press, NY.

"AIDS", Gelman, D., et al., Newsweek/Aug. 12, 1985, pp. 20–29.

"A Promising AIDS Prophylactic Therapy", Medical World News/Aug. 26, 1985, p. 74.

"AIDS: The Emerging Ethical Dilemmas", Arnold S. Relman and Mathilde Krim, Hasting Center Report, Special Supplement, Aug., 1985.

"Vaccinated Monkeys Protected in AIDS Test", Los Angeles Times, Sep. 7, 1986, Part II, p. 5.

"Spotlight on New AIDS Drugs", Medical World News, Mar. 11, 1985, pp. 60, 62.

Blaser, M. J. JAMA 255(4) Jan. 24/31 1986 "Insect-Borne Transmission of AIDS" pp. 463–464.

*Primary Examiner*—Nathan M. Nutter
*Attorney, Agent, or Firm*—Poms, Smith, Lande & Rose

[57] ABSTRACT

A method for the treatment of human disease conditions associated with HTLV infection is disclosed which is effective both as a treatment for HTLV infected individuals as well as a prophylactic treatment. The method comprises the step of hyperimmunizing a human patient with polio virus through the repeated administration of an effective dosage of polio vaccine until an effective immune response is obtained.

11 Claims, No Drawings

METHOD FOR THE EFFECTIVE TREATMENT OF DISEASE CONDITIONS IN HUMANS ASSOCIATED WITH HTLV-III INFECTION

This is a continuation of application Ser. No. 243,198, filed on Sept. 8, 1988, now abandoned, which is a continuation of application Ser. No. 907,363, filed on Sept. 16, 1986, now abandoned.

FIELD OF THE INVENTION

The present invention is directed to a method for the effective treatment of a variety of human diseases proximately caused by or associated with infection by members of a family of human T-lymphotropic retroviruses. More specifically, the present invention is directed to a prophylactic method and method for curing disease conditions in human patients which are proximately caused or associated with infection by human T-cell leukemia, lymphotropic viruses (HTLV) through the restoration of the integrity of the infected individual's immune system in general and specifically against retroviruses of the HTLV family. These disease conditions include acute lymphocytic leukemia (ALL), adult T-cell leukemia/lymphoma (ATLL), hairy cell leukemia, multiple sclerosis, acquired immune deficiency syndrome (AIDS), AIDS related complex (ARC), and pre-AIDS conditions.

BACKGROUND OF THE INVENTION

Several members of a family of human T-lymphotropic retroviruses (HTLV) have been isolated by researchers and are strongly associated with a variety of human disease conditions. Known in the art as the HTLV family of T4 tropic retroviruses, these retroviruses are known to cause T-cell proliferation leukemia, T-cell depletion, and immunosuppression in infected humans. Subgroup Q HTLV-I is the putative pathogen in T-cell proliferation and leukemia. Subgroup HTLV-II induces T-cell proliferation in vitro but its role in disease is currently unclear. Subgroup HTLV-III has recently been identified as the putative causal agent of AIDS and is strongly associated with ARC and Pre-AIDS conditions.

More specifically, HTLV-I was isolated from a black American with an aggressive form of T-cell lymphoma and has been etiologically linked to the pathegenesis of adult T-cell leukemia/lymphoma (ATLL) and acute lymphocytic leukemia (ALL). In vitro infection with HTLV-I has been shown to alter T-cell function and, in some instances, leads to T-cell death. HTLV-II has been isolated from a patient with a T-cell variety of hairy cell leukemia. HTLV-III has been isolated from AIDS patients and pre-AIDS patients suffering from chronic generalized lymphadenopathy. Both HTLV-I and HTLV-II also have been isolated from patients with AIDS.

It should be noted that HTLV-III is also referred to as LAV. This is because the Institute Pasteur in Paris reported the isolation of a retrovirus from a patient with AIDS related symptoms and named it lymphadenopathy-associated virus (LAV). At essentially the same time Dr. Robert Gallo of the National Institute of Health, in Bethesda, Maryland, reported similar success in isolating a retrovirus from patients with or at risk from AIDS and named it HTLV-III. A later detailed analysis of the genetic structures of the two viral isolates showed them to be virtually identical.

Like all retroviruses, members of the HTLV family are viruses whose genetic material is composed of ribonucleic acid which is later transcribed into DNA by reverse transcriptase and becomes permanently incorporated into the DNA of the host's genetic material. Thereafter, the retrovirus reproduces itself by transcribing its DNA into RNA which directs the synthesis of the components of new infectious viral particles which bud out of the infected cells and initiate new cycles of infection, integration and rapid viral multiplication. Once retroviral integration into the host genetic material occurs it precludes the elimination of the viral blueprints through therapeutic means.

Cures and effective vaccination agents are presently unknown. Current treatments generally involve suppression of viral multiplication through antiviral drugs in the hope of protecting uninfected cells. Efforts are currently being directed to the development of effective vaccines which can be administered to an entire population in the hope of effectively controlling the spread of infection.

Of all the diseases engendered by HTLV subgroups, AIDS, pre-AIDS and ARC are receiving the most attention. Though AIDS is a relatively recently recognized disease, it has turned up in practically every European country as well as Africa, the Caribbean, and the United States. In spite of the fact that The Centers for Disease Control (CDC) define AIDS narrowly as an acquired immune deficiency associated with one or more of only four life-threatening opportunistic infections or Kaposi's Sarcoma, at least 12,000 cases of CDC-defined AIDS were reported by mid-1985. Moreover, both the CDC and National Institutes of Health (NIH) predict that there will be approximately 40,000 AIDS cases reported nationwide by the end of 1986. Cures and effective vaccinations are not yet in sight but are being actively explored in many laboratories. At present, the prognosis is uniformly bleak. AIDS is transmissible, always fatal, and medically uncontrollable. The current mortality rate of the disease is 50% and, up to the present, no one has been known to recover from this apparently irreversible pathological process. Officials of the NIH estimate that approximately 1,000,000 persons, nationwide, are already infected with the disease which, due to its long period of latency has yet to outwardly manifest itself as AIDS or AIDS-related diseases.

The primary targets of HTLV-III affliction in the human body are specific subpopulations of T-cells, certain lymphocytes or white blood cells called T4 lymphocytes which are "helper" and regulatory cells essential to proper immune response. In vitro, HTLV-III preferentially multiplies in and kills human T4 lymphocytes. In vivo, infected individuals exhibit an unusually low portion of T4 lymphocytes resulting in severe immune deficiency and the associated opportunistic infections and rare forms of cancer. These infections include unusual forms of pneumonia due to protozoan parasites (*pneumocystis carinii* pneumonia or PCP), thrush (a fungus infection), Burkitt's lymphoma, and Kaposi's sarcoma.

Though the CDC defined AIDS narrowly in order to ensure accurate reporting for public health surveillance purposes, it was clear from the outset that the CDC reported cases of only the more advanced stages of AIDS and that a much larger population of infected individuals with a broad range of symptoms could be observed. These symptoms range from minor non-specific symptoms and detectable HTLV-III antibodies to persistent lymphadenopathy (enlargement of lymph nodes) accompanied or not by more serious symptoms (ARC) to markedly deficient cell mediated immunity associated with infections (opportunistic or not) other than those included in the CDC definition, and other types of cancers such as lymphoma. An estimated 50,000 to 100,000 Americans show early signs of ARC which include swollen lymph glands, fatigue, malaise, fever, night sweats, diarrhea, and gradual loss of weight. Additionally, because HTLV-III also invades brain cells, a considerable number of infected individuals suffer from mental and neurological problems ranging from forgetfulness and speech impairment to tremors, seizures, and dementia.

Considerable effort is being devoted to the development of effective treatments for AIDS and pre-AIDS conditions. Laboratory screening of over 100 potential compounds has been carried out and several compounds are currently being tried on patients. These include HPA-23, Ribaviran, and Suramin. Though treatment with these compounds has produced promising results including decreased viral activity and enhanced immune function, none of these agents is close to being declared an agent that will suppress the virus with minimal toxicity for any length of time. For example, HPA-23, a tungsten-antimony derivative, has serious toxicity problems including platelet-count depression. Similarly, Suramin may cause fever and abnormal renal function. The major drawback to Ribaviran is the developmont of anemia. As a result, patients are placed on two and three week courses of treatment which, hopefully, can be repeated after adverse effects have subsided.

It is a wide spread belief among practitioners in the field that no single therapeutic agent will provide a full answer to controlling AIDS. Rather, investigators suspect effective treatment will involve administration of multiple compounds, at least one compound to eliminate the presence of the virus and additional compounds to restore immune function.

The recent emphasis on AIDS research has produced quantitative data evidencing the staggering social and personal costs of this disease. The CDC recently reported that, based upon its analysis of the 10,000 AIDS cases reported in the United States by mid-1985, the average medical costs alone, from time of diagnosis to death, are $147,000, making AIDS the most expensive infectious disease. Moreover, because the majority of AIDS patients are relatively young, the total expense to the nation including lost work is estimated by the CDC to be on the order of $5 to $6 billion. When these estimates are taken in conjunction with the fact that the CDC expects a doubling of the number of reported AIDS cases every nine months, the pressing need for resolution of the AIDS epidemic becomes manifest. Factoring in the additional personal and social costs for diseases engendered by or associated with other members of the HTLV family, further emphasizes the pressing need for a resolution of these disease conditions.

As discussed above, in addition to AIDS, retroviruses of the HTLV family are known to be responsible for at least one type of T-cell leukemia in humans and are strongly associated with other forms of the disease. Leukemia is a progressive, malignant disease of the blood forming organs marked by a distorted proliferation and development of leukocytes and their precursors in the blood and bone marrow. It is accompanied by a reduced number of erythrocytes and blood platelets which results in anemia and increased susceptability to infection and hemorrhage. Typical symptoms of leukemia include fever, pain in the joints and bones and swelling of the lymph nodes, spleen and liver. Types of leukemia are classified clinically on the basis of the duration and character of the disease (acute or chronic) the type of cell involved (myelocytic, lymphoid, or monocytic), and the increase or nonincrease in the number of abnormal cells in the blood (leukemic or aleukemic).

In acute leukemia the white cells resemble precursor or immature cells and are larger than normal. The immature cells are incapable of performing their normal immunological function. In contrast to acute leukemia, in chronic leukemia the white cells are more mature and have a limited capacity to oppose invading organisms. Additionally, white cells do not accumulate as rapidly as they do in acute leukemia.

The different types of leukemia are predominate in different age groups. For example, acute lymphocytic leukemia (ALL) occurs in young children while acute myelocytic leukemia occurs primarily in young adults. Chronic lymphoid leukemia is found primarily in persons from 50 to 70 years of age and chronic myelocytic leukemia occurs in persons between 30 to 50 years of age.

In addition to the clinical evidence for the viral etiology of various forms of leukemia, it is also known that heredity plays a role in some forms of the disease. For example, leukemia frequency is fifteen times higher among those with Down's syndrome as opposed to the population in general. Similarly, the possibility of leukemia is noticably greater in persons having identical twins with the disease.

Until recently, the evidence for a viral etiology of human leukemia was circumstantial and consisted of the finding of retrovirus-type viral particles in human leukemic tissue and the demonstration of reverse transcriptase and 70S high molecular weight RNA in human leukemia cells. The most convincing evidence for viral etiology comes from the study of adult T-cell leukemia-lymphoma (ATLL) endemic to southwestern Japan and identified in the Caribbean and southeastern United States and the recent, consistent isolation of HTLV-I from ATLL patients. This convincing evidence came from the work of Dr. Robert Gallo who, in 1978, identified a unique retrovirus in patients with mature T-cell malignancies which was shown to be a unique, exogenously acquired retrovirus far removed from any then known animal retrovirus in terms of antigenicity, amino acid sequence, and nucleic acid sequence homology. It was subsequently realized that these patients suffered from a disease identical to ATLL as described in Japan.

HTLV-I has been etiologically linked to the pathogenesis of ATLL and is known to cause T-cell proliferation in leukemia. Similarly, HTLV-II was isolated from a patient with a T-cell variant of hairy cell leukemia and is known to induce T-cell proliferation in vitro; however, its role in the disease is currently unclear. Nonetheless, it is strongly implicated in the development of human leukemia.

Currently, as with AIDS, there is no known treatment existing that can permanently cure or control leukemia. Therapeutic measures for the management of the disease are chosen according to individual patient need and include radiation therapy, corticosteroid therapy, chemotherapy using antineoplastic agents, blood platelet and granulocyte transfusions, and antibiotics.

The goals of the treatment are to rid the blood, bone marrow, and tissues of leukemic cells and to control or prevent the proliferation of malignant cells. In some cases, immunotherapy and the transplanting of bone marrow from another person may be utilized for treatment. Transfusion and replacement of blood cells may relieve the symptoms of leukemia and the antineoplastic agents temporarily destroy the leukemic cells thereby prolonging the life of the afflicted patient. Remissions are known to last as long as fifteen years or more.

Though limited cross-reactivities are present between the known subgroups of the HTLV family of T4 tropic retroviruses, Western Blotting techniques with ligates of HTLV-I, HTLV-II, and HTLV-III show that the three subgroups share distinct antigenic cross-reactivity with respect to the major envelope gene product, thereby confirming the that the three known subgroups of this family of retroviruses are immunologically related.

SUMMARY OF THE INVENTION

In view of the foregoing, it is a principle object of the present invention to provide a method for the effective treatment of human disease conditions associated with or proximately caused by infection with one or more members of the HTLV family of retroviruses.

It is a further object of the present invention to provide a method which achieves these results through the suppression of the viral infection and the restoration of the integrity of the afflicted patient's immune system. Additionally, because an immunized treatment is necessarily a vaccine, it is a further object of the present invention to provide an effective prophylactic treatment for disease conditions associated with or proximately caused by HTLV infection.

It is an additional object of the present invention to provide a methodology for the effective treatment of human disease conditions associated with HTLV infections that utilizes relatively harmless agents which can be repeatedly administered to afflicted individuals without fear of developing toxic reactions requiring the interruption of treatment.

These and other objects are achieved by the method of the present invention which progressively restores the integrity of the infected individual's immune system in general and specifically against retroviruses of the HTLV family with no known side effects. Our method has proven to be effective against both acute forms of leukemia and AIDS, having eliminated the clinical manifestations of these disease conditions in patients who previously had no hope of survival.

The method of the present invention is simple, inexpensive, harmless and can be practiced as an injunctive treatment in addition to known prior art treatments against HTLV associated disease conditions. Briefly stated, the method of the present invention comprises the step of treating an individual through hyperimmunization to polio virus over an extended period of time. The immunizing agent of choice is preferably killed polio virus in order to avoid the potential of infecting an immunosuppressed HTLV afflicted individual with polio. A variety of realtively standard dosages of such polio vaccinating agents are contemplated as being within the scope of the invention, preferably ranging from approximately 0.5 cc to approximately 2.0 cc. The hyperimmunization step comprises the repeated administration of such effective dosages of polio vaccine, preferably administered every other day. Weekly or twice weekly administrations of polio vaccine are also contemplated as being within the scope of the present invention as well as daily single or multiple administrations of the vaccine. Those skilled in the art will appreciate that patients can be repeatedly dosed with the preferred polio vaccine without harm or toxic reaction.

A further understanding of the method of the present invention will be provided to those skilled in the art from the following detailed description.

DETAILED DESCRIPTION

Retroviruses of the human T-cell leukemia/lymphotropic family are now strongly associated with a variety of serious disease conditions in humans. Various forms of leukemia including acute lymphocytic leukemia (ALL) and adult T-cell leukemia/lymphoma (ATLL) as well as AIDS, AIDS-related complex (ARC) and pre-AIDS conditions are now strongly associated with specific subgroups of this family of T-cell lymphotropic retroviruses. Subgroup HTLV-I is known to cause T-cell proliferation in leukemia and is strongly associated with ALL and ATLL. Subgroup HTLV-II has been shown to induce T-cell proliferation in vitro and has been associated with a T-cell variant of hairy cell leukemia. Subgroup HTLV-III is strongly associated with AIDS, ARC, and pre-AIDS and is commonly believed to be the proximate cause thereof. Both HTLV-I and HTLV-II have been isolated from cultured T-cells of patients with AIDS. Multiple sclerosis (MS) is also thought to be associated with one or more members of the HTLV family of retroviruses.

This current understanding of the viral etiology of these diseases has been made possible by the recent advances in the isolation and identification of viruses in general. This was not the situation in the middle 1960's when it was observed that case rates for ALL were less than what would normally be expected following an outbreak of poliomyelitis. This observation led one of us (Pitts) to include hyperimmunization to killed poliomyelitis vaccine in the therapeutic regimen of a seemingly hopeless case of ALL in a boy 9 years of age. This patient had evidenced central nervous system and testicular involvement, discouraging hematological findings and had suffered one recurrence after an initial remission following then standard treatment for this disease. At that time, survival rates following recurrence of ALL after remission were essentially zero. However, this patient has now survived 19 years after the initial diagnosis with no treatment other than polio hyperimmunization in accordance with the present invention during the past 13 years. After 9 years of treatment, this patient's bone marrow examination improved from "complete replacement by lymphoblasts" to "normal with a few atypical lymphoblasts."

During this time period the significance of these results was difficult to interpret due to the lack of a sufficient understanding of the viral causes of leukemia. The recent understanding of the involvement of HTLV subgroups in leukemia coupled with the recent discovery and identification of HTLV-III as the causal agent in AIDS led us to duplicate our original methodology on a terminally ill AIDS patient as further experimental verification of our invention. This individual was suffering from a full case AIDS infection including Kaposi's sarcoma and opportunistic thrush fungus infection, having lost over 60 lbs. and presenting a T4 lymphocyte count of only 40. After 2½ months of treatment in accordance with the method of the present invention involving hyperimmunization to polio virus, all evidence of Kaposi's Sarcoma and thrush fungus disappeared. Moreover, the patient regained his lost weight and presented a T4 lymphocyte count of 64.

Armed with this recent confirmation of the efficacy of our methodology with respect to the treatment of AIDS, in conjunction with our long-term results in the effective treatment of leukemia and the recent understanding of the shared antigen and cross-reactivity of the known subgroups of HTLV we are now able to conclude that our method provides an effective long-term treatment for human disease conditions associated with HTL retroviruses and to propose a mechanism explaining its operation. We offer this explanation empirically on the basis of the results we have observed and do not wish to be rigorously bound thereby.

Members of the HTL retrovirus family, like other retroviruses are composed of a single strand of ribonucleic acid and utilize the host cells' reverse transcriptase to produce single-stranded DNA from the infective RNA agent which becomes permanently incorporated into the DNA of the host cell's genetic material. Conversely, poliovirus (of which there are three serotypes designated types 1, 2, and 3) is a single-stranded DNA virus. Based upon our observations we propose that poliovirus carries one or more antigenic determinants sufficiently analogous to a corresponding antigenic determinant common in the transcribed DNA of the three known subgroups of HTL retrovirus to impart antigenic cross-reactivity between antibodies to poliovirus and HTL viruses. Thus, by sequentially enhancing a patient's immunity to poliovirus through the method of the present invention it is possible to develop patient immunity to HTL viruses. Moreover, by restoring the integrity of the immune system with respect to the HTLV family of retroviruses, the integrity of the patient's immune system in general is enhanced through the elimination of the immunosuppressive T-lymphotropic retroviruses. The treated patient then is able to effectively ward off opportunistic and other infections through essentially normal cellular and humoral immune responses. As a result, both the underlying viral infection and associated disease conditions are effectively treated and resolved in infected individuals. Additionally, because an immunized treatment is necessarily a vaccine, the method of the present invention is also an effective prophylactic treatment in noninfected individuals.

Thus, stated in its broadest terms, the method of the present invention treats and resolves human disease conditions associated with HTL viruses by restoring the integrity of the immune system through the step of hyperimmunizing the patient infected by one or more of the HTLV subgroups with poliovaccine. Hyperimmunization is achieved by repeatedly administering an immune system restoration effective dosage of polio vaccine to the individual infected by HTLV or prior to infection as a prophylactic treatment. The appropriate immune system restoration effective dosage is administered at least once per week and preferrable is administered more often.

For example, a preferred exemplary embodiment of the present invention achieves hyperimmunization to poliovirus through repeatedly administering an effective dosage on alternate days. It is also contemplated as being within the scope of the present invention to administer an effective dosage of polio vaccine on a daily basis as well as administering multiple dosages on a daily basis. Thus, the method of the present invention is not limited to weekly administrations or administrations every other day.

A preferred polio vaccine for practicing the method of the present invention comprises killed poliovirus. Monovalent as well as polyvalent combinations of all three subtypes of polioviruses are contemplated as being within the scope of the present invention. Killed polioviruses are preferred as it is feared that administering attenuated polioviruses to immunosuppressed patients will produce polio in such patients. A preferred killed poliovirus vaccine is Salk vaccine though other killed poliovirus vaccines are contemplated as being within the scope of the present invention.

Exemplary dosages of polio vaccine which are effective at restoring an infected patient's immune system will preferably range from approximately 0.5 cc to approximately 2.0 cc. An exemplary preferred immune system restoration effective dosage is 1.0 cc of Salk or like vaccine.

After the infected patient's condition has improved or the non-infected patient exhibits the desired degree of hyperimmunity, the dosage and rate of its administration can be adjusted to what are effectively maintenance levels of administration. For example, after initial immunotherapy of twice weekly administrations of Salk vaccine, the interval between administrations can be increased to once weekly or bi-weekly administrations. We feel that maintenance dosages should be administered at least once per month, most likely for the remainder of the patient's life. However, it is also contemplated as being within the scope of the present invention to eliminate the maintenance period and discontinue the treatment after achieving hyperimmunity or the restoration of infected patient immune system integrity. Nonetheless, the administration of at least monthly maintenance dosages is preferred in order to prevent the occurrence or recurrence of disease conditions associated with HTLV infection.

Those skilled in the art will appreciate that Salk vaccine and other killed polio vaccines will be administered by injection. However, unlike known polio vaccination techniques wherein killed poliovirus is administered in three separate injections spaced one month apart to develop immunity to polio, the method of the present invention hyperimmunizes the individual infected with HTL virus or as a prophylactic treatment for non-infected individuals through frequent repeated administration of the killed polio vaccine. In this manner incremental immunization is achieved as the treated patient will respond slightly to each immunizing injection. The repeated hyperimmunizing injections eventually develop sufficient antibody levels for normal immune system function in infected individuals or for prophylactic action in non-infected individuals. What is more, the method of the present invention provides the added benefit of developing immunity to the various subgroups of the HTLV family as well.

It will also be appreciated that killed poliovirus vaccines do not produce the undesirable side effects commonly associated with known treatments for HTLV infection. Thus, the hyperimmunization method of the present invention can be continued for extended periods of time without fear of the development of undesirable complications necessitating cessation or interruption of the treatment.

The present invention is further illustrated by the following non-limiting examples. These examples are included to further illustrate the present invention and are not intended to restrict the scope of the invention in any manner.

EXAMPLE 1

A juvenile male patient aged 9 years and 10 months (52 inches in height, 68 pounds in weight) was diagnosed as having acute lymphocytic leukemia (ALL). He initially complained of shortness of breath, headaches and long bone pains and later developed physical findings including extreme pallor, weakness, rapid respiration, tachycardia, hepatosplenomegaly, generalized lymphadenopathy, tenderness over all long bones and pelvis, testicular enlargement and a slightly stiff neck with complaints of headaches on anteflexion. Complete blood count (CBC) revealed Hb-5.8 g%; Hct-18%; Wbc-30,936/cmm; platelets-92,000/cmm; differential-41 lymphoblasts and 59 abnormal lymphocytes, with anisocytosis poikilocytosis, microcytosis and hypochromasia of Rbc noted in his peripheral blood smear. Bone marrow examination showed complete replacement by lymphoblasts and skeletal X-ray survey revealed leukemic infiltration with periosteal elevations of long bones and ischium. After conventional anti-leukemic therapy with Prednisone and 6-Mercaptopurine, a complete remission was rapidly obtained. CBC showed Hb-11.5 g%; Hct-36; Wbc-2,743; platelets33,000/cmm; differential-26 segs; 73 lymphs, 1 mono; retics-0.4%. Physical examination was unremarkable and bone marrow showed complete remission with moderately severe megaloblastic changes.

Shortly thereafter he was given intrathecal methotrexate and developed chemical meningoencephalomyelitis characterized by hyperpyrexia, extreme headaches, photophobia, opisthotonous, nausea and vomiting. His temperature remained well above 102° F. for more than a week until his distressing state gradually improved. He was then vigorously treated with Prednisone on a weekly basis together with Vincristine and Daunamycin intravenously at weekly to bi-weekly intervals for several months. Bone marrow examination at monthly intervals were normal except for many lymphocytes and prolymphocytes and some lymphoblasts and the megaloblastic changes also noted in leukopenic peripheral smears where Wbc ranged between 1,000 and 7,000 and Hb ranged between 7 and 12g%. For seven months following he was given immunotherapy with BCG innoculations at weekly intervals. At the end of this time he reported continued testicular enlargement and leukemic relapse was confirmed by testicular biopsy and bone marrow examination. Thereafter vigorous treatment was instituted which included testicular and CNS radiation, Prednisone, Vincristine and Daunamycin and Methotrexate. At this time his prognosis was fatal in accordance with normal experience with ALL.

However, he was also treated in accordance with the method of the present invention wherein he was administered 1 cc killed polio vaccine subcutaneously twice weekly as immunotherapy. This treatment continued for approximately nine years until the dosage interval was increased to space the injections at intervals of approximately 6 months. Throughout this time he continued to have bone marrow, peripheral blood and physical examinations at roughly three month intervals and his last bone marrow examination was interpreted as normal with a few atypical lymphoblasts.

In contrast to the usually fatal prognosis, this patient has been active in various vigorous physical activities and has suffered only minor injuries, occasional infectious ailments, and infrequent migraine headaches.

EXAMPLE 2

A male physician aged 40 years was diagnosed as having AIDS. He was constantly bedridden and his physical findings included a weight loss of 60 pounds, oral and rectal thrush, multiple Kaposi Sarcoma lesions and an OKT4 lymphocyte count of 40 per mm$^3$.

In accordance with the teachings of the present invention, the patient was intracutaneously injected with 2 ml Salk polio vaccine every other day. After six weeks of this treatment alone, he reported that he began to feel well and became more active. Over the course of an additional four weeks of treatment comprising intracutaneous injections of 2 ml Salk polio vaccine on alternative days, he reported considerable improvement including the disappearance of the thrush infection and Karposi's lesions as well as regaining all lost weight. Additionally, he became considerably more active and began jogging daily. At that time his OKT4 lymphocyte count had increased to 64 lymphocytes per mmc.

As evidenced by the foregoing examples, the method of the present invention is effective as a treatment for disease conditions in humans associated with HTLV infection. Moreover, because the method of the present invention is an immunized treatment, it will necessarily be effective both as a prophylactic treatment or vaccine as well as for treating infected individuals. What is more, in addition to immunizing against HTLV infection, the method of the present invention also restores immunocompetence in general. Having thus described exemplary embodiments of the method of the present invention, it should now be apparent to those skilled in the art that various modifications, adaptations and equivalent methods may be made in view thereof which will follow in the scope and spirit of the present invention. For example, different polio vaccines may be utilized in place of the Salk vaccine disclosed and the frequency of administration and dosage may be varied as well. Accordingly, the scope of the present invention is defined and limited only by the following claims.

What is claimed is:

1. A method for the effective treatment of human disease conditions associated with HTLV-III, said method comprising the steps of:
   hyperimmunizing a human patient infected with HTLV-III through the repeated administration of an effective dosage of killed polio vaccine; and 2. The method of claim 1 wherein said dosage is repeatedly administered to said human patient at least once per week.

3. The method of claim 1 wherein said dosage is repeatedly administered to said human patient at least once every other day.

4. The method of claim 1 wherein said dosage is repeatedly administered to said human patient at least once per day.

5. The method of claim 1 wherein said dosage is repeatedly administered to said human patient more than once per day.

6. The method of claim 1 wherein said polio vaccine is Salk vaccine.

7. The method of claim 1 wherein said dosage of killed polio vaccine ranges from approximately 0.5 ml to 2.0 ml.

8. The method of claim 1 wherein said disease condition is Kaposi's sarcoma.

9. The method of claim 1 wherein said disease condition is a decreasing T-lymphocyte cell count.

10. A method for the effective treatment of Kapsoi's sarcoma associated with HTLV-III infection, said method comprising the steps of:

hyperimmunizing an HTLV-III infected patient having Kaposi's sarcoma through the repeated administration of an effective dosage of killed polio vaccine; and repeating said hyperimmunization on at least a monthly basis.

11. A method for the effective treatment of a declining T-lymphocyte cell count associated with HTLV-III infection, said method comprising the steps of:

hyperimmunizing an HTLV-III infected patient having a decreasing T-lymphocyte cell count through the repeated administration of an effective dosage of killed polio vaccine; and repeating said hyperimmunization on at least a monthly basis.

* * * * *